(12) United States Patent
 Burriesci et al.

(10) Patent No.: US 11,109,962 B2
(45) Date of Patent: Sep. 7, 2021

(54) BIOPROSTHETIC HEART VALVE

(71) Applicant: UCL Business PLC, London (GB)

(72) Inventors: Gaetano Burriesci, London (GB);
 Benyamin Rahmani, London (GB);
 Guerard Byrne, London (GB);
 Christopher Mcgregor, Callander (GB)

(73) Assignee: UCL Business PLC, London (GB)

( * ) Notice: Subject to any disclaimer, the term of this patent is extended or adjusted under 35 U.S.C. 154(b) by 90 days.

(21) Appl. No.: 16/317,347

(22) PCT Filed: Jul. 13, 2017

(86) PCT No.: PCT/GB2017/052073
 § 371 (c)(1),
 (2) Date: Jan. 11, 2019

(87) PCT Pub. No.: WO2018/011592
 PCT Pub. Date: Jan. 18, 2018

(65) Prior Publication Data
 US 2019/0298515 A1    Oct. 3, 2019

(30) Foreign Application Priority Data
 Jul. 13, 2016   (GB) ..................................... 1612180

(51) Int. Cl.
 *A61F 2/24*    (2006.01)
 *B65B 11/10*   (2006.01)
 *A61L 27/36*   (2006.01)

(52) U.S. Cl.
 CPC .......... *A61F 2/2415* (2013.01); *A61F 2/2412* (2013.01); *A61F 2/2418* (2013.01);
 (Continued)

(58) Field of Classification Search
 CPC ............ A61F 2/24; A61F 2/2409–2418; A61F 2/2475; A61F 2250/0069–007; A61F 2240/001; A61F 2/2415
 See application file for complete search history.

(56) References Cited

U.S. PATENT DOCUMENTS 4,172,295 A   10/1979 Batten
4,666,442 A    5/1987 Arru et al.
(Continued)

FOREIGN PATENT DOCUMENTS

EP    0155245       5/1990
EP    2404574 A1    1/2012

OTHER PUBLICATIONS

United Kingdom Application No. 1612180.8, Search Report dated Dec. 21, 2016, 3 pages.
(Continued)

*Primary Examiner* — Rebecca S Preston
(74) *Attorney, Agent, or Firm* — Kilpatrick Townsend & Stockton LLP

(57) ABSTRACT

Bioprosthetic heart valves and methods for fabricating bioprosthetic heart valves are provided. Biological tissue is attached to biocompatible material. The biocompatible material is folded to form a tubular structure with the attached biological tissue located on the inner surface of the tubular structure, the biological tissue forming leaflets of the heart valve. A stent is secured around the outer surface of the tubular structure. A region of the biocompatible material is cut. The biocompatible material is folded at the cut region away from the tissue and around the downstream edge of the stent and is secured to the stent's outer surface. The biocompatible material is folded at the upstream end of the tubular structure around the upstream edge of the stent and attached to the stent's outer surface so that the stent's inner
(Continued)

and outer surfaces are covered with no more than a single layer of the biocompatible material.

11 Claims, 7 Drawing Sheets

(52) U.S. Cl.
CPC ............ *B65B 11/10* (2013.01); *A61F 2/2409* (2013.01); *A61F 2220/0075* (2013.01); *A61F 2240/001* (2013.01); *A61F 2250/0069* (2013.01); *A61L 27/3604* (2013.01)

(56) References Cited

U.S. PATENT DOCUMENTS

| | | | |
|---|---|---|---|
| 5,258,023 A | | 11/1993 | Reger |
| 5,928,281 A | * | 7/1999 | Huynh ................... A61F 2/2409 623/2.14 |
| 2004/0176839 A1 | | 9/2004 | Huynh et al. |
| 2007/0067029 A1 | | 3/2007 | Gabbay |
| 2012/0089223 A1 | | 4/2012 | Nguyen et al. |
| 2015/0088250 A1 | * | 3/2015 | Zeng ..................... A61F 2/2409 623/2.12 |

OTHER PUBLICATIONS

International Preliminary Report on Patentability issued for PCT/GB2017/052073 dated Jan. 24, 2019.
International Search Report and Written Opinion issued for Application No. PCT/GB2017/052073 dated Oct. 30, 2017 (13 pages).

\* cited by examiner

BIOPROSTHETIC HEART VALVE

FIELD OF THE INVENTION

The present invention relates to heart valves, particularly to a bioprosthetic heart valve and to a method of fabrication for a heart valve with leaflets made from biological tissue.

BACKGROUND OF THE INVENTION

The four valves of the heart (tricuspid valve, pulmonic valve, mitral valve and aortic valve) are essential to maintain a unidirectional flow of blood around the chambers of the heart. Valvular disease, due to congenital defects or old age can lead to issues such as stenosis or regurgitation, placing a burden on the heart which can ultimately lead to heart failure.

The concept of implanting replacement valves is well known with implantable heart valves being available since the 1950s. Nowadays there are a great number of implantable heart valves available.

Important factors when choosing a heart valve to be implanted in a patient include: the ease of implantation; reliability/risk of failure; maximising resultant blood flow through the valve; and cost. Of the range of valves currently available, each has its own strengths and weaknesses.

Prosthetic valves comprising biological tissue in combination with a mechanical structure such as a frame (often referred to as a stent) are known and well documented. An example of such a valve can be found in U.S. Pat. No. 4,666,442. However, such valves have an intricate layered structure with several layers of biocompatible textile and biological tissue sutured to each other. Intricate suturing of multiple layers leads to an increase in potential failure points on the implant as well as an increase in manufacturing time and cost. Furthermore, the need for multiple fabric layers and biological tissue layers leads to a decreased inner diameter, resulting in an increase in the transvalvular pressure drop.

The present invention aims to address these problems by providing an improved bioprosthetic heart valve and method of fabrication thereof.

SUMMARY OF THE INVENTION

Accordingly, the present invention aims to solve the above problems by providing, according to a first aspect, a method for fabricating a bioprosthetic heart valve; the method comprising:
  providing: a sheet of biological tissue; a sheet of a biocompatible material, and a stent, the stent having an upstream edge and a downstream edge as well as an inner surface and an outer surface;
  attaching the biological tissue to the biocompatible material along a suture line;
  folding the biocompatible material to form a tubular structure with the attached biological tissue located on the inner surface of the tubular structure, the biological tissue forming the leaflets of the heart valve;
  securing the stent around the outer surface of the tubular structure such that the tubular structure extends in an upstream direction beyond the upstream edge of the stent and in a downstream direction beyond the downstream edge of the stent;
  cutting at least one region of the biocompatible material at the downstream end of the tubular structure;
  folding the biocompatible material at the cut region away from the biological tissue and around the downstream edge of the stent and securing it to the outer surface of the stent; and
  folding and attaching the biocompatible material at the upstream end of the tubular structure around the upstream edge of the stent so that the inner and outer surfaces of the stent are covered with no more than a single layer of the biocompatible material.

Compared to similar valves found in the prior art, the number of layers of biocompatible material and biological tissue located at the inner surface of the stent is reduced.

Only a single layer of biocompatible material and a single sheet of biological tissue are located within the orifice of the valve. Unlike prior art designs, the sheet of biological tissue may be present at the leaflets themselves and upstream of the leaflets. Downstream of the leaflets, the only material coating the inner surface of the stent is a single layer of biocompatible material. In some embodiments, rather than both the biological tissue and biocompatible material extending upstream of the leaflets (i.e. towards the cuff end of the prosthesis), only a single layer of the biocompatible material and no biological tissue may extend upstream of the leaflets. In this way, it is possible to reduce the potential risk of regurgitation (leakage) through a single layer of fabric covering the inner cuff end of the valve.

This advantageously increases the orifice area of the valve and therefore the hydrodynamic efficiency of the valve.

The number of steps required to fabricate the valve is reduced, particularly the number of suture sites. This not only results in simplified, more cost effective manufacturing process, but also decreases the number of potential points of failure on the valve.

Optional features of the invention will now be set out. These are applicable singly or in any combination with any aspect of the invention. In particular, all features described below in relation to the method of fabrication are equally applicable to aspect(s) of the present invention which relate to the bioprosthetic valve itself.

Optionally, the method for fabricating a bioprosthetic heart valve further comprises the step of trimming the biological tissue to create leaflets. This may be the final step of fabrication.

In some embodiments, the step of attaching the biological tissue to the biocompatible material includes the steps of:
  placing the sheet of biological tissue onto the biocompatible material; and
  stitching along the suture line.

In some embodiments a protective patch is applied along the suture line. This protective patch may be a strip of biological tissue and exists only at the site of the stitching thereby creating a double thickness of pericardium at the stitching site alone without requiring a full double layer of biological tissue which would result in an undesirable reduction in orifice area.

As an alternative, the patch may be obtained by folding and hemming the edge of the biological tissue to be stitched to the biocompatible material.

The protective extra patch of pericardium may have a width of 2-6 mm. The choice of width may depend on the prosthesis size as well as on the suture line pattern. The width may be constant along the length of the suture line or may vary in magnitude along the length of the suture line.

The stent is an annular frame which provides a support structure to the valve and enables it to be sutured in place. In some embodiments, the stent takes the form of a solid frame of a biocompatible metal or plastic. In other embodiments, the stent could be formed from biocompatible wire.

In some embodiments of the present invention, the downstream edge of the stent is scalloped, the scalloped edge defining a plurality of posts with concave sections there between.

In some embodiments, the suture line extends along a profile which matches the profile of the scalloped edge. The suture line could be any attachment mechanism capable of attaching one biocompatible material to another biocompatible material along a line, particularly a line with a shaped profile such as a scalloped profile. It is envisaged that the attachment along such a suture line could be formed by conventional suturing, i.e. a row of stitches. However, other suitable biocompatible mechanisms could be used such as a biocompatible adhesive.

In some embodiments (not shown), the upstream edge of the stent may also be scalloped, to create an undulated base to match the native anatomy.

In some embodiments, the step of cutting at least one region of the biocompatible material at the downstream end of the tubular structure comprises:
 cutting a region of the biocompatible material located in between each of the concave portions to form a flap of biocompatible material at the inner surface of each post of the stent. The cuts may extend along the direction of flow through the valve.

In some embodiments, the step of folding the biocompatible material at the cut region away from the biological tissue comprises folding the biocompatible material around each post and suturing the flap of biocompatible material to itself at the outer surface of the post so as to cover the entire post in no more than one layer of biocompatible material.

In some embodiments, the biocompatible material provided has an initial shape which is rectangular. The biological tissue which is sutured to the biocompatible material may also be provided in a form which has a rectangular shape. In other embodiments, the biological tissue may be pre-shaped to exhibit a scalloped edge at the upstream end of the fabric.

In some embodiments, the step of folding the biocompatible material at the upstream end of the tubular structure around the upstream edge of the stent includes creating a cuff of biocompatible material at the upstream edge of the stent.

The cuff may be formed from a rolled portion of the biocompatible material.

In some embodiments, the biocompatible material is a biocompatible fabric. This biocompatible material may take the form of any textile which is biocompatible.

In other embodiments, the biocompatible material is itself a biological tissue. That is to say, the device is fabricated by:
 providing: a first sheet of biological tissue; a second sheet of a biological tissue, and a stent, the stent having an upstream edge and a downstream edge as well as an inner surface and an outer surface;
 attaching the first sheet of biological tissue to the second sheet of biological tissue along a suture line;
 folding the second sheet of biological tissue to form a tubular structure with the attached first sheet of biological tissue located on the inner surface of the tubular structure, the first sheet of biological tissue forming the leaflets of the heart valve;
 securing the stent around the outer surface of the tubular structure such that the tubular structure extends in an upstream direction beyond the upstream edge of the stent and in a downstream direction beyond the downstream edge of the stent;
 cutting at least one region of the second sheet of biological tissue at the downstream end of the tubular structure;
 folding the second sheet of biological tissue at the cut region away from the first sheet of biological tissue and around the downstream edge of the stent and securing it to the outer surface of the stent; and
 folding and attaching the second sheet of biological tissue at the upstream end of the tubular structure around the upstream edge of the stent so that the inner and outer surfaces of the stent are covered with no more than a single layer of the second sheet of biological tissue.

In this way, aside from the stent, the prosthetic valve could be made entirely from biological tissue such as animal pericardium. Where a valve is fabricated from pericardium, more than one type of pericardium could be used.

According to a second aspect of the present invention there is provided a bioprosthetic heart valve comprising:
 a stent, the stent having an upstream edge and a downstream edge as well as an inner surface and an outer surface;
 a single biocompatible material layer folded around the stent to cover the entire inner and outer surfaces of the stent by no more than a single layer of biocompatible material; and
 leaflets formed from biological tissue, the biological tissue of the leaflets attached to the biocompatible material by a suture line at the downstream edge of the stent.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

A first embodiment of a fabrication method according to the present invention is described below with reference to FIGS. 1 to 5.

In an initial step, a sheet of biological tissue 1 and a sheet of a biocompatible material 2 are provided. In the embodiment shown, each of the sheets has a rectangular shape. However, it is envisaged that alternative shapes could be provided, such as those shown in FIGS. 6a-6d.

The biological tissue typically takes the form of a sheet of human or animal pericardium, typically decellularised. Suitable types of animal pericardium include, but are not restricted to, porcine or bovine pericardium. In some embodiments, the biological tissue is tissue-engineered; that is to say it forms a scaffold material seeded with stem cells. This scaffold material may be formed from decellularised animal or human tissue, or from synthetic biomaterials. Such synthetic biomaterials may be bioresorbable or biostable.

The biocompatible material may take the form of a suitable biocompatible fabric such as: a PET and/or PTFE fabric; compact or porous polymeric sheets; and patches made from polymeric fibres (e.g. by electrospinning). As discussed above, in some embodiments, the biocompatible material is a biological tissue. This may take the form of the same type of biological tissue as the leaflets, or a different biological tissue if different properties are desired.

The biological tissue is attached to the biocompatible material along a suture line. In the embodiment shown, the suture line has a scalloped profile.

A stent, 4 is also provided. In the embodiment shown the stent takes the form of a solid frame, typically made from a biocompatible plastic such as acetal resins (e.g. Delrin®), Polyether ether ketone (PEEK) or a biocompatible metal such as titanium, or cobalt based alloys. Alternatively frames of a biocompatible wire could also be used.

Figure 3:
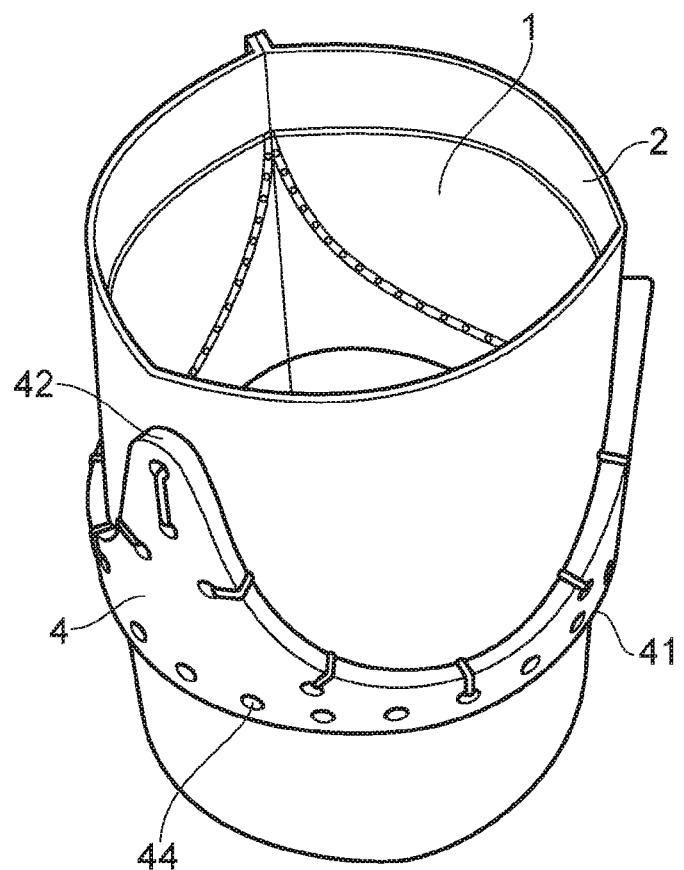
FIG. 3 shows a schematic diagram of a further step in the method for fabricating a bioprosthetic heart valve.
Figure 4:
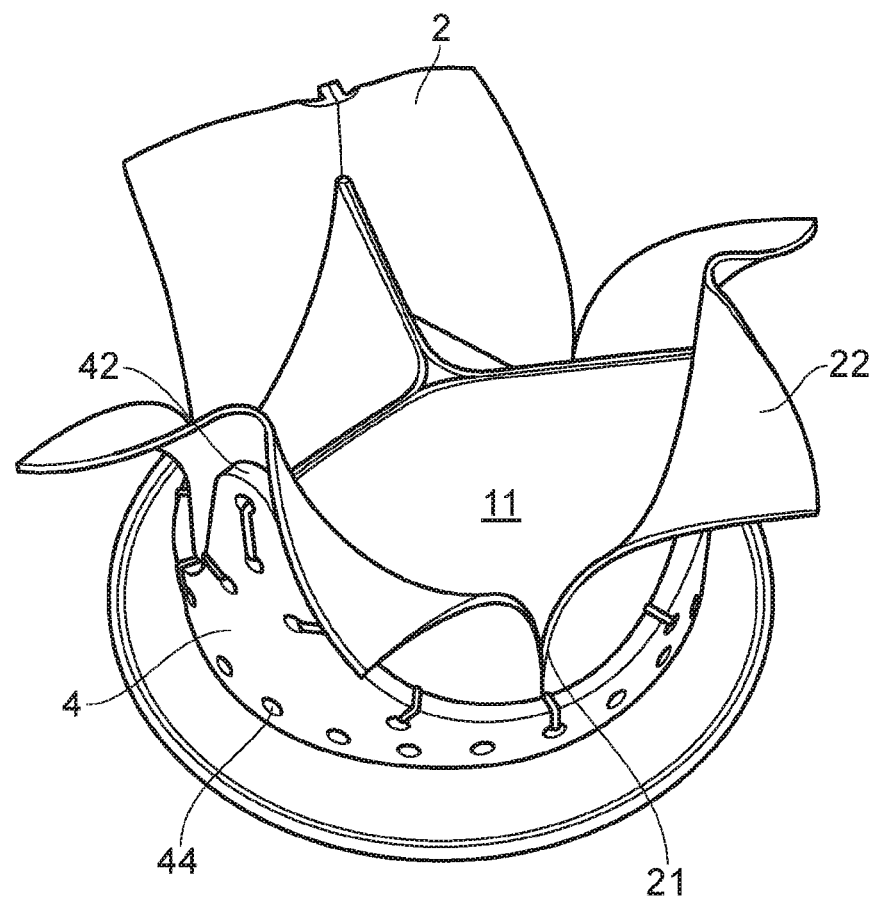
FIG. 4 shows a schematic diagram of a further step in the method for fabricating a bioprosthetic heart valve.

The stent comprises an upstream edge 41 and a downstream edge 42 as well as an inner surface (not visible in FIGS. 3 and 4) and an outer surface (visible in FIGS. 3 and 4).

Figure 2:
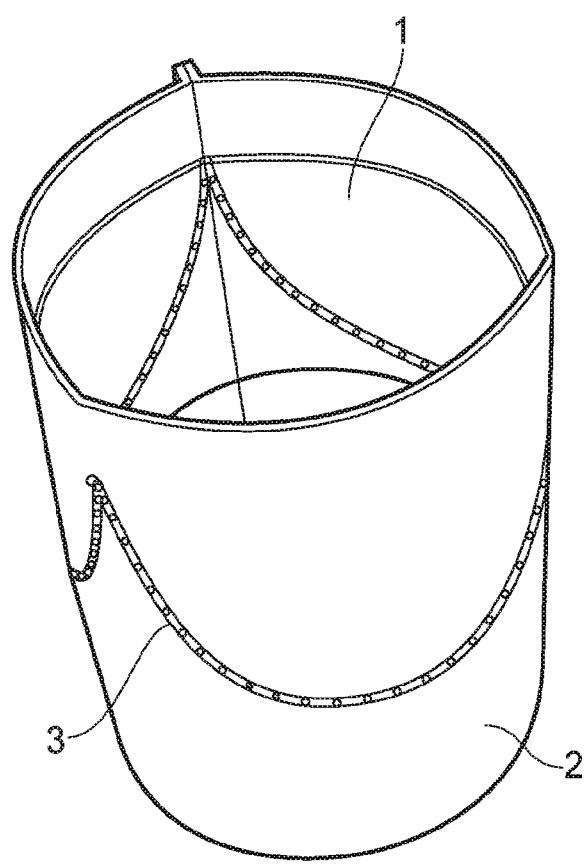
FIG. 2 shows a schematic diagram of a further step in the method for fabricating a bioprosthetic heart valve.

In a subsequent fabrication step, the biocompatible material 2 is folded to form a tubular structure with the attached biological tissue 1 located on the inner surface of the tubular structure. As shown in FIG. 2, a first side of the (rectangular) sheet of biocompatible material is sutured to an opposite side of the sheet, the suturing extending along the length of the respective sides to seal the inner and outer surfaces of the tubular structure along its entire length in the direction of flow.

The biological tissue, located on the inner surface of the biological tissue forms the leaflets 11 of the heart valve. Since the biological tissue is attached to the biocompatible material only at the suture line, the biological tissue located downstream of the suture line can move away from the biocompatible material towards the central axis of the tubular structure thereby forming the leaflets 11 of the valve.

In a further fabrication step depicted in FIG. 3, the tubular structure is placed inside the stent 4 and the stent is secured to the outer surface of the tubular structure such that the tubular structure extends in an upstream direction beyond the upstream edge of the stent and in a downstream direction beyond the downstream edge of the stent. There must be sufficient biocompatible material above and below the stent to cover the upstream edge 41 and downstream edge 42 of the stent respectively.

The stent of FIGS. 3 and 4 has a flat upstream edge and a scalloped downstream edge. The scalloped edge 42 consists of a plurality of posts with concave portions located in-between posts. When in situ, these concave portions prevent obstruction of the coronaries.

A plurality of reference holes 44 are located along both the upstream edge and the downstream edge, the holes extending between the inner and outer surface of the body of the stent. The tubular structure is sutured to the inner surface of the stent via the reference holes which are located along the downstream edge. Since the suture line 3 has the same profile as the downstream edge 42 of the stent, the suturing through the reference holes will lie upstream of the scalloped suture line.

In a further fabrication step shown in FIG. 4, the biocompatible material 2 of the tubular structure is cut. This cutting occurs in regions of the biocompatible material at the downstream end of the tubular structure, more particularly in the regions of the biocompatible material located in between each of the concave portion of the scalloped stent 4 to form a flap of biocompatible material at the inner surface of each post of the stent.

The cuts 21 extend along the direction of flow through the valve. In the embodiment shown, the cuts are shown as simple slits. However, in other embodiments (not shown), the cuts may have a "finger like" shape, giving rise to flaps with curved edges which follow the scalloped profiled structure of the stent, extending outwards from the downstream edge 42 of the stent by a given amount along the entire downstream edge.

Once cuts 21 have been made in the biocompatible material, the biocompatible material flaps left behind at the cut region are folded in a direction away from the biological tissue and around the downstream edge of the stent and securing it to the outer surface of the stent.

Each flap of biocompatible material extends either side of a respective post and is folded around both sides of said post before being sutured to itself at the outer surface of the post. This suturing may take the form of a vertical line 23 of stitching extending along each respective post along the direction of flow through the valve.

In this way, a single sheet of biocompatible material has been used to cover the entire inner surface and outer surface of the stent as well as both its upstream and downstream edges, 41, 42. The inner and outer surfaces of the stent are therefore covered with no more than a single layer of the biocompatible material.

Once the biocompatible material has been folded around the posts of the downstream edge 42 of the stent and secured to itself at the outer surface of the stent; the remaining uncovered portions of the stent are covered by folding the biocompatible material at the upstream end of the tubular structure around the upstream edge 41 of the stent and attaching to the outer surface of the stent so that the inner and outer surfaces of the stent are covered with no more than a single layer of the biocompatible material.

The biocompatible material is sutured 25 to itself and can be better secured to the stent suturing through the reference holes 44 of the stent, including reference holes at the upstream edge as well as some reference holes located at the concave portions of the downstream edge.

Excess biocompatible material at the upstream edge of the stent is rolled and stitched 26 to form a cuff 41 for attachment and location purposes, the cuff extending radially outwards from the covered stent. The cuff can be cushioned by stuffing it with soft biocompatible material.

Figure 5:
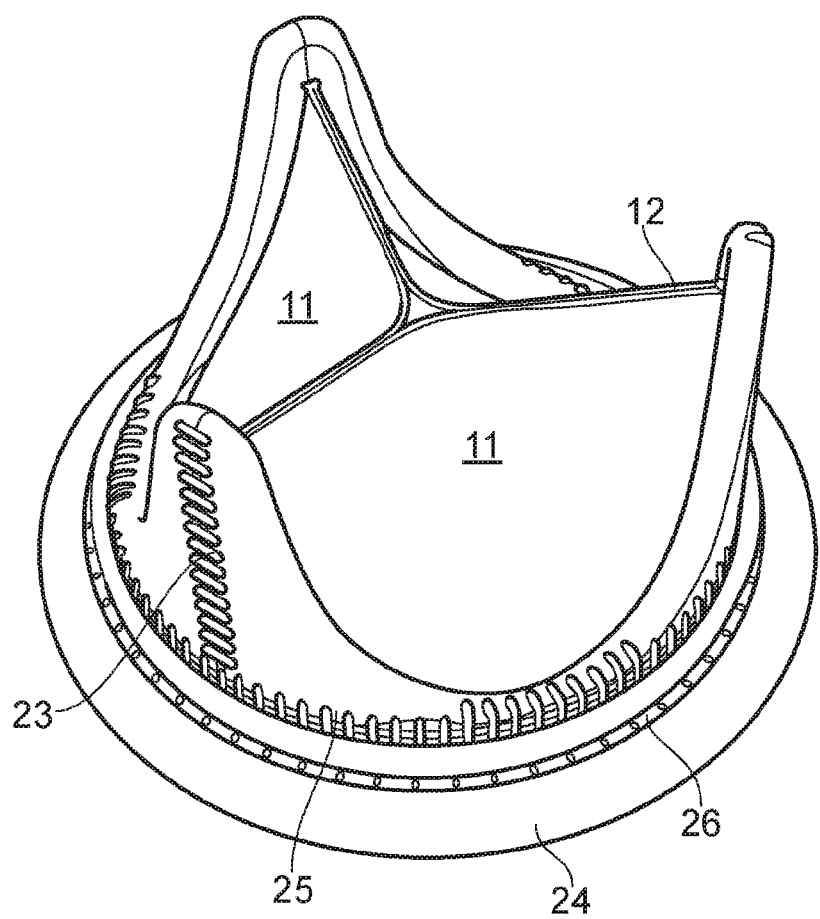
FIG. 5 shows a schematic diagram of a fabricated bioprosthetic heart valve.

In a final step, the biological tissue 11 of the leaflets is trimmed at the downstream side to produce the desired leaflet edges 12. The completed device, with trimmed leaflets is shown in FIG. 5.

FIGS. 6a to 6d depict the initial step of attaching the biological tissue 1 to the biocompatible material 2. As with previous embodiments, the biocompatible material 2 may take the form of a biocompatible fabric or may take the form of a second sheet of biological tissue.

Figure 1:
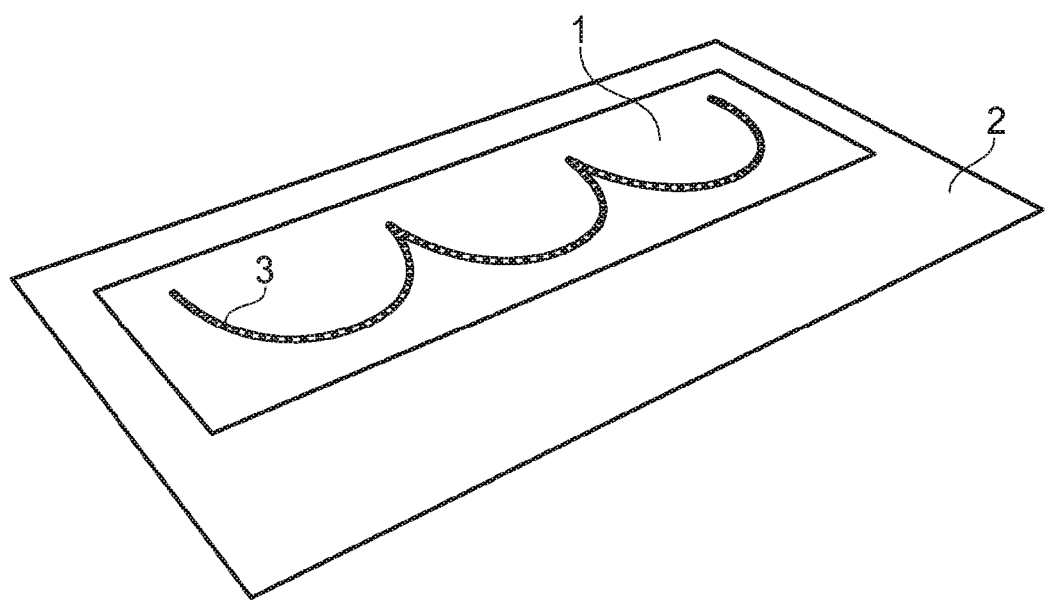
FIG. 1 shows a schematic diagram of an initial step in the method for fabricating a bioprosthetic heart valve.
Figure 6:
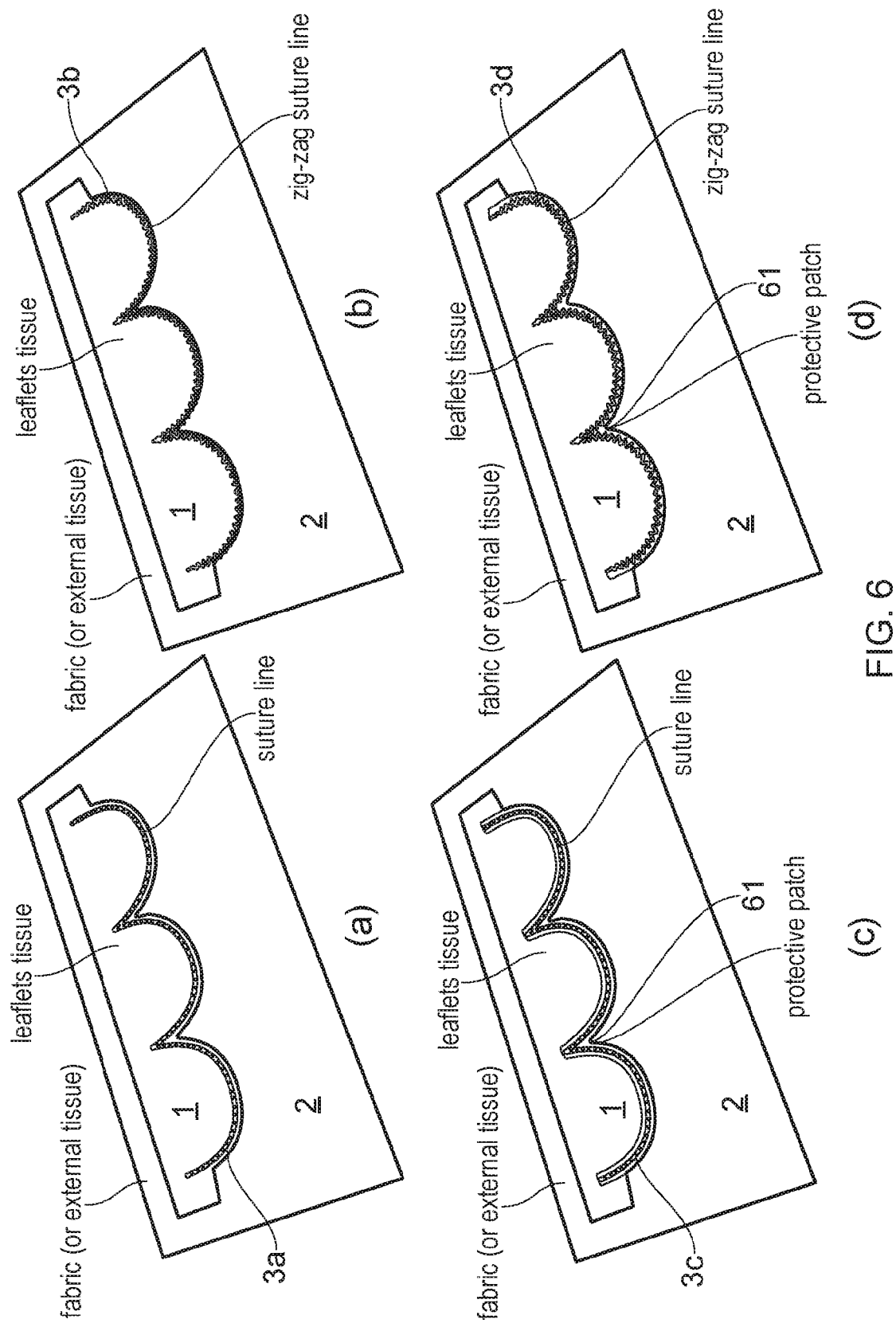
FIGS. 6a-6d each show a schematic diagram of example of alternative initial steps in alternative embodiments of the method for fabricating a bioprosthetic heart valve.

The embodiment of FIG. 6a differs from the embodiment described in FIG. 1 in that the biological tissue 1 is cut to exhibit a scalloped edge on the upstream side in proximity of the suture line created to attach the biological tissue 1 to the biocompatible material 2.

The embodiment of FIG. 6*b* differs from that of FIG. 6*a* in that the suture line 3*b* uses zig-zag stitching rather than backstitch.

The embodiments of FIGS. 6*c* and 6*d* differ from the embodiments of 6*a* and 6*b* respectively in that a protective patch 61 is applied along the suture line. This protective patch takes the form of a strip of biological tissue or biocompatible material located at the opposite surface of the biological tissue to the surface in contact with the biocompatible material 2. The protective patch exists only at the site of the stitching without requiring a double layer of biological tissue at any location other than at the suture line.

FIGS. 7*a* to 7*d* depict the initial step of attaching the biological tissue 1*a* to the biocompatible material 2*a*. As with previous embodiments, the biocompatible material 2*a* may take the form of any biocompatible fabric or may take the form of another biocompatible material such as a second sheet of biological tissue.

Figure 7:
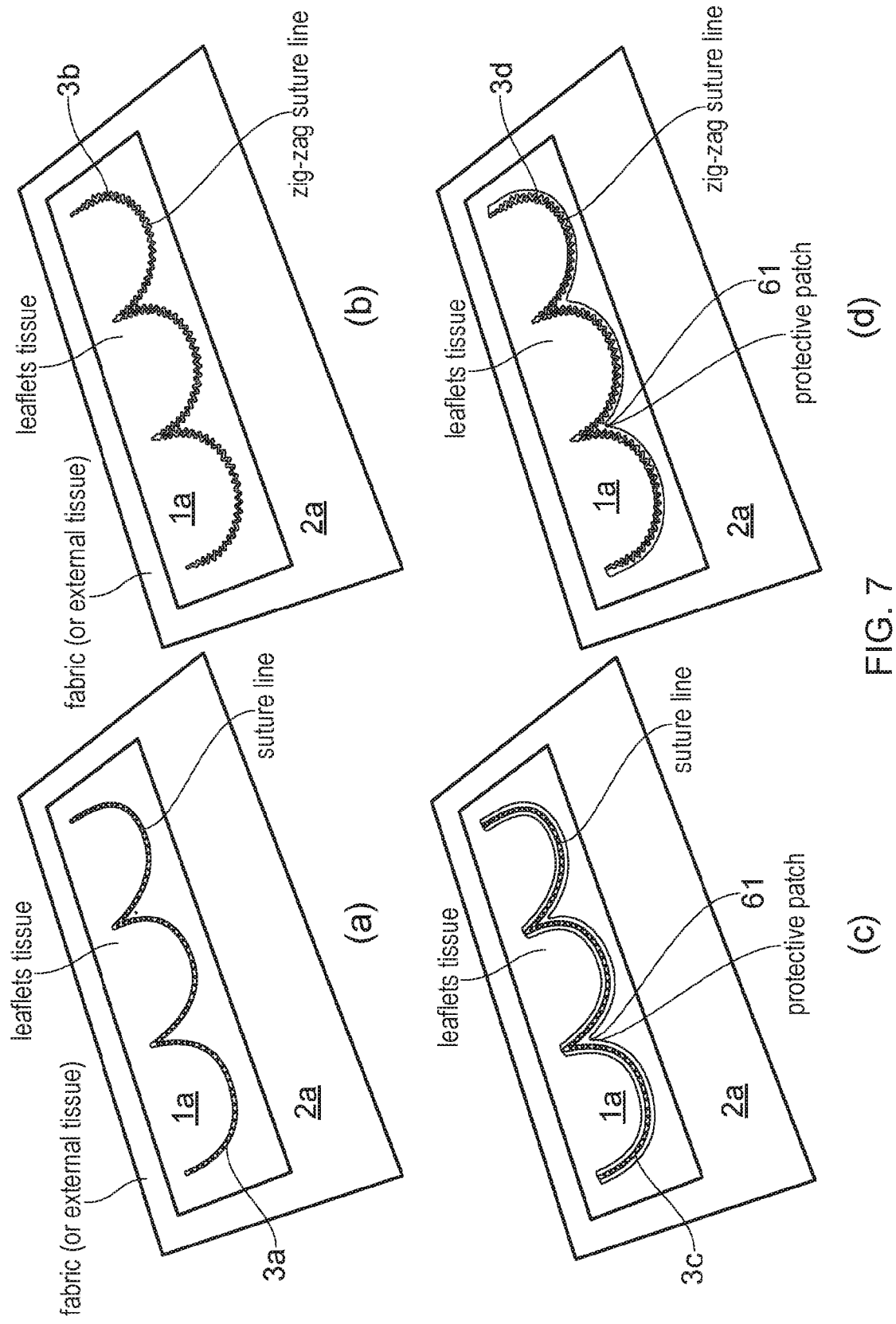
FIGS. 7a-7d each show a schematic diagram of further examples of alternative initial steps in alternative embodiments of the method for fabricating a bioprosthetic heart valve.

The embodiment of FIG. 7*a* differs from the embodiment described in FIG. 6*a* in that the biological tissue 1*a* is not cut to exhibit a scalloped edge on the upstream side. Instead, a portion of biological tissue is located upstream of the suture line 3*a*.

This upstream portion of biological tissue may be put to use in at least one of two ways.

Firstly, the biological tissue can be trimmed in proximity of the upstream edge 41 of the stent and sutured to the biocompatible material.

Secondly, the upstream portion of biological tissue may be used instead of the biocompatible material to cover the stent upstream of the leaflets (not shown), in which case, the biocompatible material would instead be trimmed upstream of the leaflets (i.e. 'below' the leaflets in the orientation shown in FIGS. 1 to 5). In this way, the total number of layers covering the inner surface of the stent is still kept to a minimum.

The embodiment of FIG. 7*b* differs from that of FIG. 7*a* in that the suture line 3*b* uses zig-zag stitching rather than backstitch.

The embodiments of FIGS. 7*c* and 7*d* differ from the embodiments of 7*a* and 7*b* respectively in that a protective patch 61 is applied along the suture line. This protective patch takes the form of a strip of biological tissue or biocompatible material located at the opposite surface of the biological tissue to the surface in contact with the biocompatible material 2. The protective patch exists only at the site of the stitching without requiring a double layer of biological tissue at any location other than at the suture line.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A method for fabricating a bioprosthetic heart valve, the method comprising:
   providing: a sheet of biological tissue, a sheet of a biocompatible material, and a stent, the stent having an upstream edge and a downstream edge as well as an inner surface and an outer surface;
   attaching the biological tissue to the biocompatible material along a suture line;
   folding the biocompatible material to form a tubular structure with the attached biological tissue located on an inner surface of the tubular structure, the biological tissue forming leaflets of the heart valve;
   securing the stent around an outer surface of the tubular structure such that the tubular structure extends in an upstream direction beyond the upstream edge of the stent and in a downstream direction beyond the downstream edge of the stent;
   cutting at least one region of the biocompatible material at a downstream end of the tubular structure;
   folding the biocompatible material at the at least one cut region away from the biological tissue and around the downstream edge of the stent and securing it to the outer surface of the stent; and
   folding and attaching the biocompatible material at an upstream end of the tubular structure around the upstream edge of the stent so that the inner and outer surfaces of the stent are covered with no more than a single layer of the biocompatible material.

2. The method of claim 1, further comprising the step of trimming the biological tissue to create the leaflets.

3. The method of claim 1, wherein the step of attaching the biological tissue to the biocompatible material includes the steps of:
   placing the sheet of biological tissue onto the biocompatible material; and
   stitching along the suture line.

4. The method of claim 3, wherein the downstream edge of the stent is scalloped, the scalloped edge defining a plurality of posts with concave sections therebetween.

5. The method of claim 4, wherein the suture line extends along a profile which matches the profile of the scalloped edge.

6. The method of claim 4, wherein the step of cutting at least one region of the biocompatible material at the downstream end of the tubular structure comprises:
   cutting a region of the biocompatible material located in between each of the concave sections to form a flap of biocompatible material at an inner surface of each post of the stent.

7. The method of claim 6, wherein the step of folding the biocompatible material at the at least one cut region away from the biological tissue comprises:
   folding the flap of biocompatible material around each post and suturing the flap of biocompatible material to itself at an outer surface of the post so as to cover the entire post in no more than one layer of biocompatible material.

8. The method of claim 1, wherein the biocompatible material provided has an initial shape which is rectangular.

9. The method of claim 1, wherein the step of folding the biocompatible material at the upstream end of the tubular structure around the upstream edge of the stent includes creating a cuff of biocompatible material at the upstream edge of the stent.

10. The method of claim 1, wherein the biocompatible material is a biocompatible fabric.

11. The method of claim 1, wherein the biocompatible material is a biological tissue.

* * * * *